United States Patent [19]

Crossley et al.

[11] Patent Number: 4,923,991
[45] Date of Patent: May 8, 1990

[54] QUINOLINE DERIVATIVES

[75] Inventors: Roger Crossley, Reading; Kenneth Heatherington, Burnham, both of United Kingdom

[73] Assignee: John Weyth & Brother Limited, Maidenhead, England

[21] Appl. No.: 285,909

[22] Filed: Dec. 16, 1988

Related U.S. Application Data

[63] Continuation-in-part of Ser. No. 571,972, Jan. 18, 1984, Pat. No. 4,837,329.

[30] Foreign Application Priority Data

Jan. 19, 1983 [GB] United Kingdom ................. 8301377

[51] Int. Cl.$^5$ ............................................ C07D 215/04
[52] U.S. Cl. ....................................... 546/152; 546/93; 546/101; 546/153; 546/155; 546/174; 546/178; 546/180; 546/181
[58] Field of Search ................. 546/152, 180, 93, 101, 546/155, 174, 178, 181, 153

[56] References Cited

U.S. PATENT DOCUMENTS

| 4,022,792 | 5/1977 | Albertson et al. | 546/101 |
| 4,046,895 | 9/1977 | Curran et al. | 546/93 X |
| 4,085,215 | 4/1978 | Curran et al. | 546/93 X |

FOREIGN PATENT DOCUMENTS

| 1463665 | 2/1977 | United Kingdom . |
| 1463670 | 2/1977 | United Kingdom . |
| 1465651 | 2/1977 | United Kingdom . |

OTHER PUBLICATIONS

Hahn et al., Roczniki Chemii 38, 989 (1964).

Rosen et al., J. Org. Chem. 42, 47 (1977).

*Primary Examiner*—David B. Springer
*Attorney, Agent, or Firm*—Richard K. Jackson

[57] ABSTRACT

The invention provides a compound of formula III

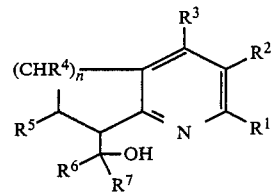

or an acid addition salt thereof, wherein $R^1$, $R^2$, $R^3$, $R^4$, $R^5$, $R^6$ and $R^7$ are the same or different and represent hydrogen or lower alkyl, cycloalkyl, lower aralkyl or phenyl radicals any of which radicals may be substituted by lower alkyl, lower alkoxy or trifluoromethyl or $R^2$ and $R^3$ taken together, form a 5, 6 or 7 membered saturated ring, $R^4$ and $R^5$ may also represent lower alkoxy or cycloalkoxy, n is 1, 2 or 3 and, if more than one $R^4$ radical is present the $R^4$ radicals may be the same or different and esters of carboxylic acids with the hydroxy group shown, wherein $R^1$, $R^2$, $R^3$, $R^4$, $R^5$ and n are as defined above, with the provisos that (1) $R^6$ and $R^7$ are other than hydrogen when $R^1$, $R^2$, $R^3$, $R^4$ and $R^5$ are all hydrogen and (2) $R^6$ and $R^7$ are not both methyl when $R^4$ is methyl.

Compounds III are intermediates for other compounds with anti-ulcer or anti-secretory activity. Some of the compounds III are intermediates for anti-inflammatory agents.

5 Claims, No Drawings

QUINOLINE DERIVATIVES

The invention relates to quinoline derivatives and is a continuation-in-part of our copending U.S. Ser. No. 571 972 filed 18 Jan. 1984, now U.S. Pat. No. 4,837,329.

In our copending U.S. Ser. No. 571972 we have disclosed a process for preparing dihydro compounds of formula I

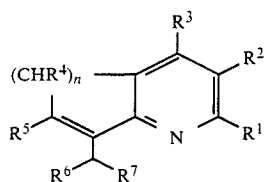

and acid addition salts thereof, wherein $R^1$, $R^2$, $R^3$, $R^4$, $R^5$, $R^6$ and $R^7$ are the same or different and represent hydrogen, or alkyl, cycloalkyl, aralkyl, or aryl radicals any of which radicals may by substituted, or $R^1$ and $R^2$ taken together or $R^2$ and $R^3$ taken together, form a 5, 6 or 7 membered ring which may be saturated or unsaturated and substituted or unsubstituted, $R^4$ and $R^5$ may also represent alkoxy, or cycloalkoxy, n is 1, 2 or 3 and, if more than one $R^4$ radical is present the $R^4$ radicals may be the same or different which process comprises re-arranging a compound of formula II

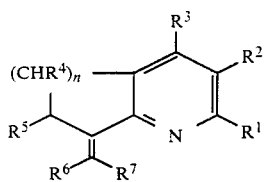

wherein $R^1$, $R^2$, $R^3$, $R^4$, $R^5$, $R^6$, $R^7$ and n are as defined above.

The re-arrangement of compound II to compound I may be carried out under acidic or basic conditions. Examples of acid catalysts which may be used are organic acids such as carboxylic acids e.g. lower alkylcarboxylic acids such as acetic acid, inorganic acids such as phosphoric acid, or polyphosphoric acids, Lewis acids e.g. boron trifluoride, zinc chloride or acid anhydrides e.g. acetic anhydride. Alternatively a noble metal catalyst, e.g. a Pt or Pd catalyst may be used, optionally in the presence of a weak base such as sodium acetate or a heterogeneous or homogeneous catalyst, e.g. $PdCl_2(PhCN)_2$, $RhCl[(C_6H_5)_3P]_3Ru_3(CO)_{12}$ or $IrCl(CO)[(C_6H_5)_3P]_2$ Preferably the rearrangement is carried out in the presence of acetic acid, a noble metal catalyst in the presence of a base, or a Lewis acid.

The above mentioned acids may be used to prepare acid addition salts of compounds of the invention.

When any of $R^1$, $R^2$, $R^3$, $R^4$, $R^5$, $R^6$ or $R^7$ is an alkyl radical it is preferred that this is a lower alkyl radical of 1 to 6 carbon atoms which may have a straight or branched chain e.g. methyl, ethyl, n- and iso-propyl and n-, s- and t-butyl. When $R^4$ or $R^5$ is an alkoxy radical it is preferred that the radical is lower alkoxy in which the alkyl portion has 1 to 6 carbon atoms and is as defined above, for an alkyl radical.

When any of $R^1$, $R^2$, $R^3$, $R^4$, $R^5$, $R^6$ or $R^7$ is a cycloalkyl radical such radicals having from 4 to 6 carbon atoms are preferred i.e. cyclobutyl, cyclopentyl or cyclohexyl. If $R^4$ or $R^5$ is cycloalkoxy the cycloalkyl portion of this group may be as just described for a cycloalkyl group. An aralkyl group may be an arylalkyl group in which the alkyl portion is as described herein for an alkyl group. Preferred aralkyl groups are those having from 7-12 carbon atoms.

When any of $R^1$, $R^2$, $R^3$, $R^4$, $R^5$, $R^6$ or $R^7$ is an aryl group it is preferably phenyl or substituted phenyl (substituted by e.g. alkyl, alkoxy or trifluoromethyl). The aryl portion of an aralkyl group may be substituted as described for a phenyl group.

The present invention concerns intermediates for compounds of formula II, which intermediates have formula III.

The starting materials of formula II may be prepared by dehydration of the corresponding compounds of formula III

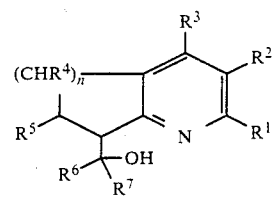

wherein $R^1$, $R^2$, $R^3$, $R^4$, $R^5$, $R^6$, $R^7$ and n are as defined above.

The dehydration may be carried out with usual dehydration agents e.g. polyphosporic acid or with acetic anhydride, (in which case an intermediate acetylated derivative may be formed, from which acetic acid is eliminated to give the compound of formula II).

Some compounds of formula III are novel and are included in the invention. These are compounds of formula III and their acid addition salts and esters of carboxylic acids wherein $R^1$, $R^2$, $R^3$, $R^4$, $R^5$ and n are as defined above in connection with formula I and $R^6$ and $R^7$ are other than hydrogen when $R^1$, $R^2$, $R^3$, $R^4$, and $R^5$ are all hydrogen and $R^6$ and $R^7$ are not both methyl when $R^4$ is methyl.

Preferred compounds of formula III are the sub group of formula IIIA

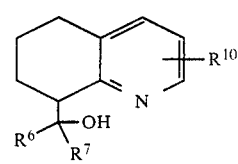

or an acid addition salt thereof wherein $R^{10}$ is lower alkyl and $R^6$ and $R^7$ are selected from hydrogen, lower alkyl, cycloalkyl, or lower aralkyl radicals. Examples are [8R*]-5,6,7,8,-tetrahydro-8-([2S*]-2-(2-hydroxy-1-phenyl)propyl)-3-methylquinoline; 5,6,7,8-tetrahydro-8-(2-(2-hydroxy)propyl-3-methylquinoline and their acid addition salts.

The compounds of formula III may be prepared by treatment of a compound of formula IV

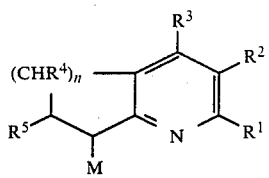

wherein $R^1$, $R^2$, $R^3$, $R^4$, $R^5$ and n are as defined in connection with formula I, and M is hydrogen, an alkali metal (e.g. sodium, potassium or lithium) or MgHal, where Hal is chlorine, bromine or iodine, with a carbonyl compound of formula V

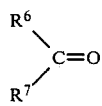

wherein $R^6$ and $R^7$ are as defined in connection with formula I, with the proviso that when $R^6$ and $R^7$ are both hyrogen then M is hydrogen.

It has been reported by Hahn and Epsztajn, Roczniki Chemie, 1964, 38, 989 that treatment of VIa or VIb

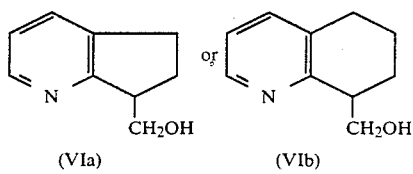

with polyphosphoric acid gives the corresponding methylene compounds VIIa and VIIb

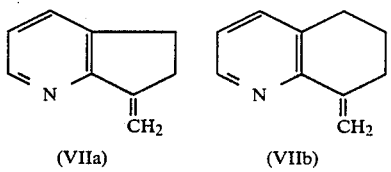

exclusively with no corresponding methyl isomer being formed. We have surprisingly found that compounds of formula I wherein $R^6$ and $R^7$ are hydrogen, can be obtained by treatment of a compound of formula IV wherein M is hydrogen with formaldehyde (which may be in the form of paraformaldehyde) in the presence of an organic acid anhydride, e.g. acetic anhydride. It is believed that an intermediate compound of formula III wherein $R^6$ and $R^7$ are both hydrogen is formed initially, this dehydrates to give a compound of formula II wherein $R^6$ and $R^7$ are hydrogen and the compound of formula II rearranges to give a compound of formula I wherein $R^6$ and $R^7$ are hydrogen.

Previously compounds of formula I were relatively inaccessible—see Rosen and Weber J Org. Chem. 1977, 42, 47–50 who obtained 8-methyl-5,6-dihydroquinoline by pyrolysis of 1-methyl-1(α-pyridinyl)-1,3-butadiene. However pyrolysis is not a satisfactory method of preparation especially for molecules carrying a variety of substituents.

Compounds of formula I may be used as intermediates for the preparation of the corresponding compounds of formula XIV

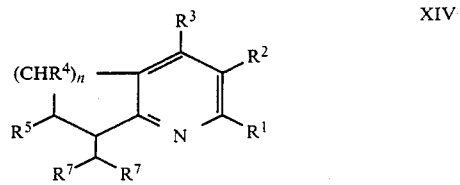

Compounds of formula XIV are intermediates for other compounds with anti-ulcer or anti-secretory activity e.g. the compounds of UK Patent Specification No. 1432378. Some compounds of formula II where $R^6$ and/or $R^7$ are phenyl or substituted phenyl may also possess anti-inflammatory activity as determined by standard test procedures.

The invention is illustrated by the following Examples.

EXAMPLE 1

3,8-Dimethyl-5,6,7,8-tetrahydroquinoline

A mixture of 3-methyl-5,6,7,8-tetrahydroquinoline (100 ml) paraformaldehyde (30 g) and acetic anhydride (100 ml) was heated at reflux for 30 hours. The residue was distilled to give a mixture of starting tetrahydroquinoline and 3,8-dimethyl-5,6-dihydroquinoline (40 g) bp. 126°–180°/15 mm. Chromatography on silica gel (500 g, Woëlm active, 100–200) using di-isopropyl ether gave 3,8-dimethyl-5,6-dihydroquinoline (22 g).

A solution of the dihydroquinoline (22 g) in ethanol (200 ml.) was hydrogenated over 10% palladium on carbon (1 g) at 25° and 1 atmosphere. After the theoretical uptake had occurred (1.5 hours) the catalyst was removed by filtration, the filtrate evaporated and the residue distilled to give the title tetrahydroquinoline (22 g) bp. 124°/15 mm $C_{11}H_{15}N$ requires: C, 81.9; H, 9.4; N, 8.7%. Found: C, 81.9, H, 9.1, N, 8.3%

The catalyst in this example is a mixture of acetic anhydride and acetic acid, the acetic acid being produced in situ.

EXAMPLE 2

Compound Present

The reaction described in Example 1, 1st paragraph, was followed in a time course experiment, samples being taken at intervals and composition analysed by glc. (Pye 104 C20M T=200°) Results were as follows:

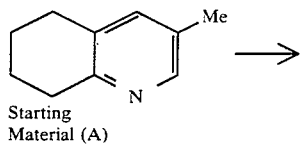

Starting Material (A)

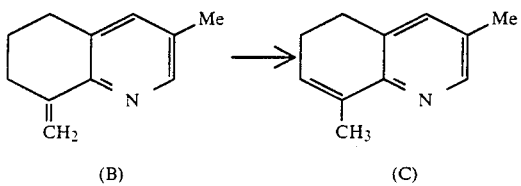

(B)          (C)

| Time | | | |
|---|---|---|---|
| 1½ hours | 20% | 66% | 7% |
| 2½ hours | 21% | 61% | 11% |
| 4¼ hours | 22% | 51% | 20% |
| 6½ hours | 23% | 42% | 26% |
| 30 hours | 22% | 0 | 68% |

EXAMPLE 3

The reaction described in Example 1, 1st paragraph, was repeated employing various catalysts. The results are shown in the following table (for structures of compounds B and C—see Example 2).

| Isomerisation of Compound B to Compound C using various Catalysts. | | |
|---|---|---|
| Catalyst/Reaction Conditions | Reaction time (hours) | Percentage of Compound C |
| $CH_3CO_2H$, reflux | 30 | 100 |
| NaOAc, 5% Pd—C, EtOH, reflux | 21.6 | 85.4 |
| $BF_3 \cdot Et_2O$, dioxan, reflux | 24 | 83 |
| PPA, 100° | 1.5 | 76[a] |
| $H_3PO_4$, $H_2O$, reflux | 21.6 | 25.1 |
| $ZnCl_2$, dioxan, reflux | 30 | 22.5 |
| $(CH_3CO)_2O$, reflux | 30 | 5 |
| KOH, EtOH, 22° | 30 | 5 |

[a]Severe decomposition of compound C was observed after 2 hours.
PPA = Polyphosphoric acid

EXAMPLE 4

[8R*]-5,6,7,8-tetrahydro-8-([2S*]-2-(2-hydroxy-1-phenyl)propyl)-3-methylquinoline.

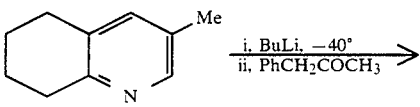

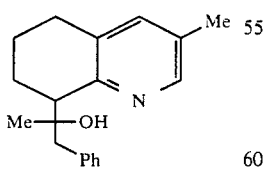

To a mixture of 5,6,7,8-tetrahydro-3-methylquinoline (20 g) and toluene (100 ml) was added 1.63 molar n-BuLi in hexane (93 ml) at −40° C. The resulting anion solution was added to a mixture of phenylacetone (50 ml) and toluene (100 ml) at −40° C. The solution was allowed to warm to room temperature and the excess n-BuLi was quenched by adding 2N HCl (90 ml). The excess solvent was removed by evaporation. The resultant aqueous mixture was basified with saturated aqueous $NaHCO_3$ solution and extracted with EtOAc (3×100 ml). The extracts were dried ($MgSO_4$) and the solvent removed by evaporation. The mixture of products was separated by chromatography[$SiO_2$; cyclohexane—$CH_3CO_2CH_3$ (4:1)]. Upon removal of the solvent by evaporation the product crystallised to give the title compound (2.25 g), m.p. 99°–101° C. (Found: C, 81.1; H, 8.1; N, 4.7. $C_{19}H_{23}NO$ requires C, 81.1; H, 8.2; N, 5.0%).

EXAMPLE 5

[8R*]-5,6,7,8-tetrahydro-8-([2R*]-2-(2-hydroxy-1-phenyl)propyl)-3-methylquinoline

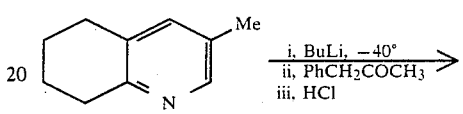

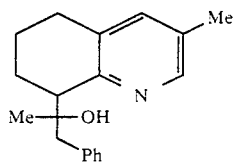

To a mixture of 5,6,7,8-tetrahydro-3-methylquinoline (20 g) and toluene (100 ml) was added 1.63 molar n-BuLi in hexane (93 ml) at −40° C. The resulting anion solution was added to a mixture of phenylacetone (50 ml) and toluene (100 ml) at −40° C. The resulting solution was allowed to warm to room temperature. The excess n-BuLi was quenched by adding 2N-HCl (90 ml). The aqueous layer was separated, basified with saturated aqueous $NaHCO_3$ solution, and extracted with $Et_2O$ (3×100 ml). The ethereal extracts were dried ($MgSO_4$) and the solvent removed by evaporation. The mixture of products was separated by chromatography [$SiO_2$; cyclohexane—methyl acetate (80:20)]. The solvent was removed by evaporation and the residue dissolved in $Et_2O$, to which an ethereal solution of HCl (50 ml) was added. The precipitate was collected by filtration, washed with $Et_2O$, and dried in vacuo to give the title compound as a hydrochloride 1½ hydrate (2.09 g) m.p. 98°–100° C. (Found: C, 66.2; H, 7.5; N, 3.9. $C_{19}H_{23}NO \cdot HCl \cdot 3/2H_2O$ requires C, 66.2; H, 7.9; N, 4.1%).

EXAMPLE 6

5,6,7,8-tetrahydro-8-(1-hydroxyethyl)-3-methylquinoline

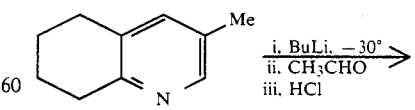

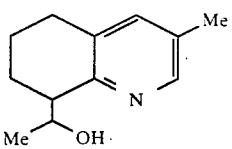

To a mixture of 5,6,7,8-tetrahydro-3-methylquinoline (20 g) and dry THF (150 ml) was added 1.63 molar n-BuLi in hexane (108 ml) at −30° C. The resulting anion solution was added to a solution of acetaldehyde (50 ml) in anhydrous THF (50 ml) at −30° C. The solution was allowed to warm to room temperature. The excess n-BuLi was quenched with 2N-HCl (20 ml). The excess acetaldehyde and solvent were removed by evaporation. The resultant aqueous mixture was basified with saturated aqueous $NaHCO_3$ solution and extracted with $Et_2O$ (3×100 ml). The ethereal extracts were dried ($MgSO_4$) and the solvent removed by evaporation. The mixture of products was separated by chromatography ($SiO_2$; EtOAc). The solvent was removed by evaporation and the residue dissolved in $Et_2O$ to which ethereal HCl (50 ml) was added. The product was removed by filtration, washed with $Et_2O$ and dried in vacuo to give the title compound as the hydrochloride ¼ hydrate (1.13 g) m.p. 172°–175° C. (Found: C, 62.4; H, 7.9; N, 6.0 $C_{12}H_{17}NO.HCl.¼H_2O$ requires C, 62.1; N, 8.0; N, 6.0%).

EXAMPLE 7

5,6,7,8-Tetrahydro-8-(2(2-hydroxy)propyl)-3-methyl-quinoline

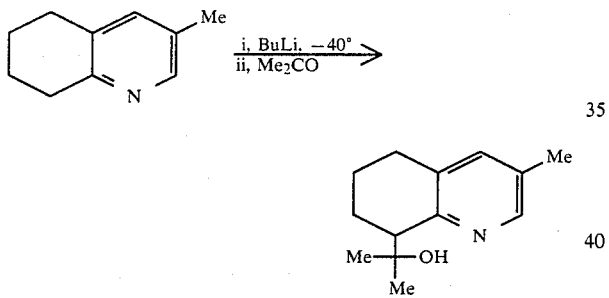

To a mixture of 5,6,7,8-tetrahydro-3-methylquinoline (23.44 g, 159 mmol) and toluene (200 ml) was added 1.63 molar n-BuLi in hexane (108 ml) at −40°. After 15 mins. the resulting anion solutio was added to a solution of acetone (100 ml) in toluene (200 ml). The solution was allowed to warm to room temperature and was treated with 2N-HCl (90 ml). The excess acetone was removed by evaporation in vacuo. The resultant aqueous mixture was basified with saturated aqueous $NaHCO_3$ solution and extracted into $Et_2O$ (3×100 ml). The ethereal extracts were dried ($MgSO_4$) and the solvent removed by evaporation in vacuo. The mixture of products were separated by chromatography [$SiO_2$; EtOAc-petrol (1:4)] to give the free base (7.303 g, 22%) of the title compound as a red oil.

A small quantity of the free base (0.744 g) was dissolved in $Et_2O$ and treated with ethereal HCl. The product was removed by filtration, washed with $Et_2O$, and dried in vacuo to give the title compound as the hydrochloride, m.p. 140°–144°. (Found: C, 63.2; H, 8.3; N, 5.5. $C_{13}H_{19}NO.HCl.¼H_2O$ requires C, 63.4; H, 8.4; N, 5.7%).

EXAMPLE 8

5,6,7,8-Tetrahydro-3-methyl-8-(2-propylidene)quinoline

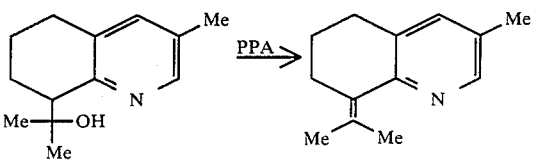

Experimental Details

A mixture of 5,6,7,8-tetrahydro-8-(2(2-hydroxy)-propyl)-3-methylquinoline (3.044 g, 14.8 mmol) and polyphosphoric acid (20 g) was vigorously stirred at 80°–90° for 50 mins. and then poured into saturated aqueous $Na_2CO_3$ solution (200 ml). The aqueous solution was extracted with $Et_2O$ (2×100 ml) and the ethereal extracts dried ($MgSO_4$) and evaporated in vacuo to give an oil. Purification by column chromatography [$SiO_2$; hexane-propan-2-ol(1:1)] and bulb-to-bulb distillation gave the title compound (1.855 g, 67%) as a colourless oil, b.p. 150°–5°/0.1 mm Hg (Found: C, 83.25; H, 9.3; N, 7.5 $C_{13}H_{17}N$ requires C, 83.4; H, 9.15; N, 7.5%).

We claim:

1. A compound of formula III

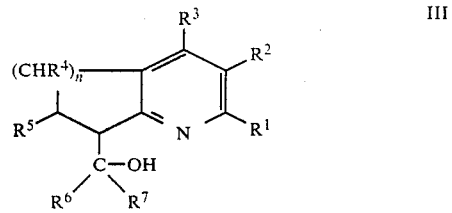

or a pharmaceutically acceptable salt thereof, wherein $R^1$, $R^2$, $R^3$, $R^4$, $R^5$, $R^6$ and $R^7$ are, independently, hydrogen, alkyl of 1 to 6 carbon atoms cycloalkyl of 4 to 6 carbon atoms, aralkyl of 7 to 12 carbon atoms or phenyl, any of which cyclic structures may be monosubstituted by alkyl of 1 to 6 carbon atoms, alkoxy of 1 to 6 carbon atoms, or —$CF_3$;

or $R^2$ and $R^3$, taken together, form a 5, 6 or 7 membered saturated carbocyclic ring;

$R^4$ and $R^5$ may also be alkoxy of 1 to 6 carbon atoms or cycloalkoxy of 4 to 6 carbon atoms;

n is one of the integers 1, 2 or 3;

and, if more than one $R^4$ group is present, the $R^4$ groups may be the same or different;

and carboxylic acid esters of the depicted hydroxy substituent;

with the provisos that (1) when $R^1$, $R^2$, $R^3$, $R^4$, and $R^5$ are all hydrogen, $R^6$ and $R^7$ are other than hydrogen, and (2) when $R^4$ is methyl, $R^6$ and $R^7$ are not both methyl.

2. A compound of formula III as claimed in claim 1, wherein n is 2 and $R^1$, $R^2$, $R^3$, $R^4$ and $R^5$ selected from hydrogen and alkyl of 1 to 6 carbon atoms.

3. A compound of formula IIIA

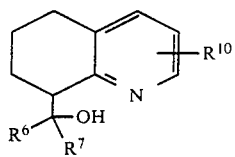

or a pharmaceutically acceptable acid addition salt thereof wherein $R^{10}$ is alkyl of 1 to 6 carbon atoms and $R^6$ and $R^7$ are selected from hydrogen, alkyl of 1 to 6 carbon atoms, cycloalkyl, or aralkyl of 7 to 12 carbon atoms.

4. [8R*]-5,6,7,8-tetrahydro-8-([2S*]-2-(2-hydroxy-1-phenyl)propyl)-3-methylquinoline, the 2R* isomer thereof, or a pharmaceutically acceptable acid addition salt thereof.

5. 5,6,7,8-Tetrahydro-8-(2(2-hydroxy)propyl-3-methylquinoline or an acid addition salt thereof.

* * * * *